United States Patent [19]
Karr et al.

[11] Patent Number: 6,093,415
[45] Date of Patent: Jul. 25, 2000

[54] SYNERGISTIC JUVENOID CHITIN SYNTHESIS INHIBITOR TERMITICIDE COMPOSITIONS

[75] Inventors: Laura L. Karr, Lebanon, Ind.; Ronald J. Sbragia, Placerville, Calif.

[73] Assignee: Dow AgroSciences LLC, Indianapolis, Ind.

[21] Appl. No.: 09/022,075

[22] Filed: Feb. 11, 1998

Related U.S. Application Data

[60] Provisional application No. 60/037,607, Feb. 12, 1997.

[51] Int. Cl.$^7$ ..................................................... A01N 25/32
[52] U.S. Cl. ......................... 424/406; 424/405; 424/409; 424/410; 424/413; 424/DIG. 11; 514/277; 514/594
[58] Field of Search .................................... 424/405, 406, 424/409, 410, 413, 414, DIG. 11; 514/277, 299, 549, 594

[56] References Cited

U.S. PATENT DOCUMENTS 5,556,883  9/1996  Thoms et al. ........................... 574/594

FOREIGN PATENT DOCUMENTS

| 86 061934 | of 1986 | South Africa . |
| WO 93 23998 | 12/1993 | WIPO . |
| WO 95 16354A | 6/1995 | WIPO . |

OTHER PUBLICATIONS

Derwent Abstract AN 89–204057, Sumitomo, "Poison Bait Tablets For Insect Pest Control—Contain Insect Juvenile Hormone Like Cpd., Insect Chitin Formation Inhibitor, Cellulose, Cereal Powder, Vegetable Oil And Sugar" 1989.

El–Guindy M, et al., "The Joint Action of Mixtures of Insecticides, or of Insect Growth Regulators and Insecticides, on Susceptible and Diflubenzuron–Resistant Strains of *Spodoptera Littoralis* Boisd", Pesticide Science, vol. 14, Jan. 1, 1983, pp. 246–252.

Ross et al., "Response Of Late–Instar *Blattella Germanica* (*Dictyoptera: Blattellidae*) To Dietary Insect Growth Regulators," Journal of Economic Entomology, vol. 83, No. 6 — 1990, pp. 2295–2305.

Nan–Yao Su et al., "Laboratory Evaluation of Two Chitin Synthesis Inhibitors, Hexaflumuron And Diflubenzuron, As Bait Toxicants Against Formosan and Eastern Subterranean Termites (*Isoptera Rhinotermitidae*)," Journal of Economic Entomology, vol. 86, No. 5 —1993, pp. 1453–1457.

Haverty et al. "Concentration–Dependent Presoldier Induction and Feeding Deterrency: Potential OF Two Insect Growth Regulators FOR Remedial Control of the Formosan Subterranean Termite (*Isoptera: Rhinotermitidae*)" Journal of Economic Entomology, vol. 82, No. 5—1989, pp. 1370–1374.

Nan–Yao Su et al, "Comparative Effects Of AN Insect Growth Regulator, S–031183, Against The Formosan Termite And Eastern Subterranean Termite (Isoptera: Rhinotermitidae)" Journal of Economic Entomology, vol. 82, No. 4—1989, pp. 1125–1129.

Faragalla et al., "Field Evaluation of the Effects of the Juvenile Hormone Analogues (JHA's) and Diflubenzuron (Dimilin) on Termites of the Genus Microcerotermes (Isopter: Termitidae) in the Central Region of Saudia Arabia" Sociobiology, vol. 11, No. 1, 1985, pp 29–37.

Robertson et al. "Joint Action of a Juvenile Hormone Analog with Benzoylphenylureas Ingested by Western Spruce Budworm, Choristoneura Occidentalis (Lepidoptera: Tortricidae)" The Canadian Entolmologist, vol. 116, 1984, pp. 1063–1068.

El–Guindy M, et al., "The Ovidical Action of Insecticides and Insect Growth Regulator/Insecticide Mixtures on the Eggs of Various Ages of Susceptible and Diflubenzuron–Resistant Strains of *Spodoptera Littoralis* Boisd.", Pesticide Science, vol. 14, Jan. 1, 1983, pp. 253–260.

*Primary Examiner*—Neil S. Levy
*Attorney, Agent, or Firm*—Carl D. Corvin; Donald R. Stuart

[57] ABSTRACT

Combinations of a chitin synthesis inhibitor (e.g. hexaflumuron, flufenoxuron, lufenuron, and dimiin) with a juvenile hormone mimic (e.g. methoprene and pyriproxyfen) afford synergistic activity against termites.

9 Claims, No Drawings

SYNERGISTIC JUVENOID CHITIN SYNTHESIS INHIBITOR TERMITICIDE COMPOSITIONS

This application claims the benefit of U.S. Provisional Application No. 60/037,607, filed Feb. 12, 1997.

FIELD OF THE INVENTION

The present invention provides synergistic termiticide compositions and methods of controlling termites using such compositions.

BACKGROUND OF THE INVENTION

Efforts to control termites within the United States cost in excess of one billion dollars per year. Termites, insects of the order Isoptera, feed mainly on cellulose-based materials, and if unchecked, can do appreciable damage to wooden buildings, certain crops, paper and other articles which contain cellulose.

Termite activity can be detected using systems where a food material, typically a cellulose containing material, is placed at a location where termite activity is suspected or likely to occur and the material periodically monitored to determine if termites are feeding on the material. In some recent efforts to monitor and control termites, once feeding activity on the cellulose containing material used at the monitoring site is observed, a slow acting toxicant is added to the material such that the termites that feed on the baited material carry the toxicant back to the termite colony thereby helping to reduce or eliminate the termite colony. Slow acting toxicants are employed so that the termites live long enough to return to the termite colony and deliver toxicant to other members of the colony via trophallaxis. In addition, trail pheromones left by the foraging termites may result in additional termites feeding on the baited material which in turn leads to additional quantities of the toxicant being carried back to the termite colony. In at least one commercial treatment scheme, when termite workers are found attacking the food material at the monitoring site, the termites are collected and placed in a bait tube wherein the termites must eat their way through a food material containing a toxicant in order to return to the termite colony. This procedure helps to ensure that termites returning to the colony induce or "recruit" other termites to feed at the bait tube.

The ideal toxicant for use in schemes to control termites using returning colony members to deliver toxicant to the colony would act slowly enough so that a significant amount of toxicant is returned to the colony, but fast enough so that the colony is eliminated quickly.

Benzoylphenylureas are known class of insecticidal compounds. Their mode of action is inhibition of chitin synthesis. Juvenile hormone mimics are another known class of insecticides. Use of 1[3,5-dicloro-4-(1,1,2,2-tetrafluoroethoxy)phenyl]-3-(2,6-difluorobenzoyl)urea (hexaflumuron) as a termiticide is disclosed in U.S. Pat. No. 5,556,883. Use of (RS)-1-[2,5-dichioro-4-(1,1,2,3,3,3-hexafluoropropoxy)phenyl]-3-(2,6-difluorobenzoyl)urea (lufenuron) as a termiticide is disclosed in WO 95/16354. Use of 1-(4-chloropnonyl)-3-(2,6-difluorobenzoyl)urea (diflubenzuron) as a termiticide is disclosed in A. A. Faragalla et al. "Field Evaluation of the Effects of the Juvenile Hormone Analogues (JHA's) and Diflubenzuron (Dimilin) on Termites of the Genus Microcerotermes (Isoptera: Termitidae) in the Central Region of Saudi Arabia," Sociobiology 1985, 11, 29–37.

The combination of a juvenile hormone mimic with a benzoylphenylurea has previously been tested against some insects other than termites, but with mixed results. Simultaneous application of the juvenile hormone analogue methoprene with 1-(4-chlorophenyl)-3-(2,6-difluorobenzoyl)urea (diflubenzuron) or (N-[trifluoromethoxy)phenyl]carbamoyl-2-chlorobenzamide in a ratio of 1:9 methoprene:benzoylphenylurea (BAY SIR 8514) was reported to give no advantage in treatment of spruce budworm, but simultaneous application of methoprene and) (N-[[[5-(4-bromophenyl)-6-methyl-2-pyrazinyl]amino]carbonyl]-2-chlorobenzamide (EL-127063) was reported to give a significant advantage. J. L. Robertson et al., "Joint Action of a Juvenile Hormone Analogue with Benzoyiphenylureas ingested by Western Spruce Budworm, Choristoneura occidentalis (Lepidoptera: Tortiricidae)" Can. Ent. 1984, 116, 1063–68.

The results of testing mixtures of diflubenzuorn/methoprene and diflubenzuorn/triprene on eggs of various ages of cotton leafworm *Spodoptora littoralis* Boisd. are reported in M. A. El-Guindy et al., "The Ovicidal Action of Insecticides and Insect Growth Regulator/Insecticide Mixtures on the Eggs of Various Ages of Susceptible and Diflubenzuron-resistant Strains of *Spodoptera littoralls* Boisd." Pestic. Sci. 1983, 14, 253–260. A strain susceptible to diflubenzuron and a strain resistant to diflubenzuron were tested. Diflubenzuorn/triprene showed an additive effect on 0–1 day old eggs of the S strain. Diflubenzuron/methoprene was reported to show moderate synergism on 0–1 day old eggs of the susceptible strain; however, the synergistic effect was replaced by an antagonistic effect for eggs 1–2 days old and eggs 2–3 days old. The diflubenzuorn/methoprene combination also showed antagonism when tested on the resistant strain.

SUMMARY OF THE INVENTION

The present invention provides a synergistic termiticide composition comprising, as active ingredients, a chitin synthesis inhibitor and a juvenile hormone mimic in a CST:JHM weight ratio of from 1:1 to 1:3.

The invention also provides a method of controlling termites which comprises delivering a composition comprising a chitin synthesis inhibitor and a juvenile hormone mimic in a CSI:JHM weight ratio of from 1:1 to 1:3 to a location where control of termites is desired.

The invention also provides a termite bait comprising, as active ingredients, a composition comprising a chitin synthesis inhibitor and a juvenile hormone mimic in a CSI:JHM weight ratio of from 1:1 to 1:3, in combination with a bait matrix.

DETAILED DESCRIPTION OF THE INVENTION

Chitin synthesis inhibitors that can be used with the invention are benzoylphenylureas of formula (I):

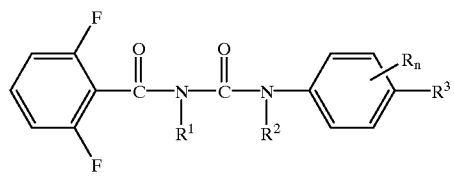

wherein $R^1$ and $R^2$ are H, methyl, or ethyl;

$R_n$ represents H, 2-fluoro, 3,5-dichloro, 2,5-dichloro, or 2-fluoro-3,5-dichloro;

$R_3$ is Cl, or $OR_4$ $R_4$ is (a) $C_nH_mF_{(2n+1-m)}$, where n is 2 to 4 and m is 0 to 2n+1;

(b) $CF=CFCF_3$ or $CF_2CF=CFCF_3$; or (c)

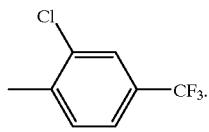

Specific benoylphenylureas that can be used with the invention include:

1-[3,5-dichloro-4-(1,1,2,2-tetrafluoroethoxy)phenyl]-3-(2,6-difluorobenzoyl)urea (hexaflumuron):

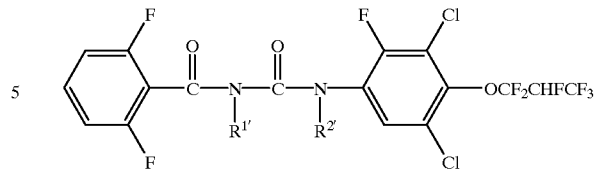

1-(4-chloropnenyl)-3-(2,6-difluorobenzoyl)urea (diflubenzuron):

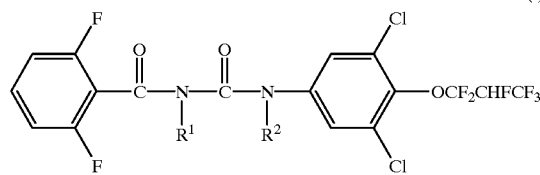

(RS)-1-[2,5-dichloro-4-(1,1,2,3,3,3-hexafluoropropoxy)phenyl]-3-(2,6-difluorobenzoyl)urea (lufenuron):

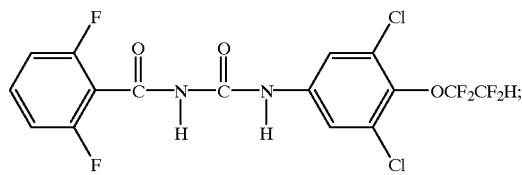

1-[4-(2-chloro-α,α,α-trifluoro-p-tolyoxy)-2-fluorophenyl]-3-(2,6-difluorobenzoyl)urea (flufenoxuron):

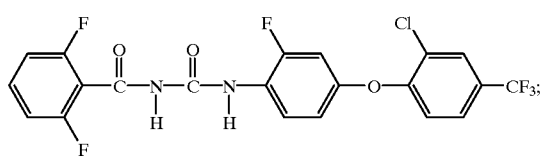

compounds of the formula

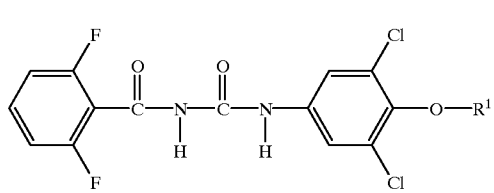

wherein $R^{1'}$ and $R^{2'}$ are H, methyl, or ethyl; compounds of the formula (I)

wherein $R^1$ and $R^2$ are H, methyl, or ethyl; and compounds of the formula (I)

wherein $R^1$ is $-CF=CFCF_3$ or $-CF_2CF=CFCF_3$.

Several of the benzoylphenylureas that can be utilized in the invention are commercially avialable, for example dimilin, hexaflumuron, diflubenzuron, and lufenuron. The benzolyphenylureas can be sythesized by well known methods. See, for example, U.S. Pat. No. 4,139,636. In general, 2,6-difluorobenzoyl isocyanate is reacted with an appropriately substituted amine in 1,2-dichoroethane under nitrogen at room temperature. Compounds wherein $R^2$ is methyl or ethyl are prepared by using an appropriately substituted secondary amine. Compounds wherein $R^1$ is methyl or ethyl can be prepared by alkylating corresponding compounds wherein $R^1$ is H.

Juvenile hormone mimics that can be used with the invention include isopropyl (E,E)-(RS)-11-methoxy-3,7,11-trimethyldodeca-2,4-dienoate (methoprene), ethyl (E,E)-(RS)-3,7,11-trlmethyldodeca-2,4-dienoate (hydroprene); and 4-phenoxyphonyl (RS)-2-(2-pyridyloxy)propyl ether (pyriproxyfen). Methoprone, hydroprone, and pyriproxyfen are commercially available compounds, and they are made using known technology. See, for example, U.S. Pat. Nos. 3,904,662, 3,912,815, 4,021,461.

The compositions of the present invention are typically used by locating monitoring/control devices, such as bait tubes and/or housings, at or near a location where termite foraging activity is expected or has been observed. The devices are monitored by periodic visual inspections or other monitoring means to detect when termites have started to feed on the composition contained in or associated with the monitoring/control devices. During the monitoring phase, to avoid the unnecessary use of toxicants, the monitoring is performed without the use of toxicants in the monitoring material; however, it is possible to use a termiticidal composition from the onset, particularly where extensive termite activity is suspected or observed. Once termites are detected and feeding established, a termiticidal composition of the present invention can be added to or substituted for the monitoring material in order to achieve termite control by reducing or eliminating the termites in the vicinity of the location where the termites feed on the termiticidal composition.

The present invention can be used to control a wide variety of termite species, including *Coptotermes formosanus, Reticulitermes flavipes, Reticulitermes hesperus, Reticulitermes virginicus, Reticuitermes tibialis*, and *Heterotermes aureus*, as well as termite species of the families (and pest genera) Mastotermitidae (Mastotermes species), Hodotermididae (Anacanthotermes, Zootermopsis species), Rhinotermitidae (Coptotermes, Heterotermes, Reticulitermes, Psammotermes, Prorhinotermes, Schedorhinotermes species), Kalotermitidae (Glyptotermes, Neotermes, Cryptotermes, Incisitermes, Kalotermes, Marginitermes species), Serritermitidae, and Termitidae (Pericapritermes, Allodontermes, Microtermes, Odontotermes, Nasutitermes, Termes, Amitermes, Globitermes, Microcerotermes species) Termopsidae (Hodotermopsis, Zootermopsis species), and other pest species of termites.

Compositions of the present invention are particularly useful in termite control methods described in WO93/23998.

Intermediate 1

2,6-difluorobenzoyl isocyanate

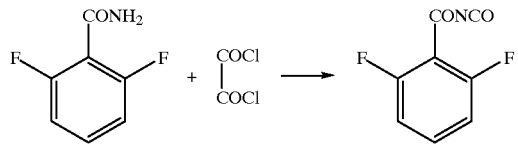

A mixture of 0.52 g of 2,6-difluorobenzamide and 0.33 ml of oxalyl chloride was stirred under reflux in 15 ml, 1,2-dichloroethane overnight. Solvent was removed under vacuum and 10 mL 1,2-dichloroethane was added. Solvent was removed under vacuum to leave the title intermediate, which could be used directly or dissolved in 1,2-dichioroethane and stored for future use.

Intermediate 2

3,5-Dichloro-4-(1,1,2,3,3,3-hexafluoropropoxy)aniline

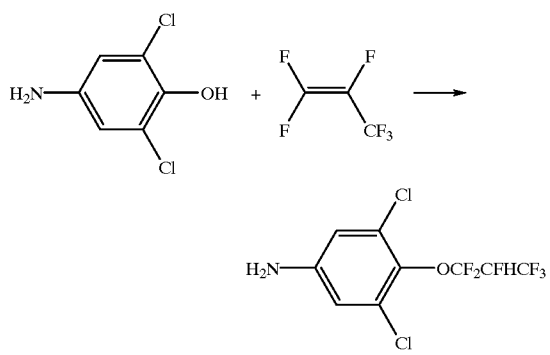

To a solution of 2.0 g of 4-amino-2,6-dichlorophenol in 40 mL tetrahydrofuran at room temperature was added 0.7 g of 87% potassium hydroxide. The mixture was warmed to 40° C. and stirred for 10 minutes, then chilled to 0° C. Hexafluoropropene was bubbled in for 5 minutes, and the mixture stirred at room temperature over night. It was then concentrated under vacuum to dryness. The residue was dissolved in 50 mL dichloromethane and washed with 20 mL brine solution. The organic layer was separated and filtered through phase separation filter paper and then concentrated under vacuum to an oil. This was diluted with 50 mL dichloromethane and 50 mL heptane and re concentrated to give 3.05 g of 3,5-Dichloro-4-(1,1,2,3,3,3-hexafluoropropoxy)aniline as a brown oil. Proton and $^{19}F$ nmr spectra were consistent with the proposed structure.

Intermediate 3

3,5-Dichloro-4-(1,1,2,3,3,3-hexafluoropropoxy)-N-ethyl aniline

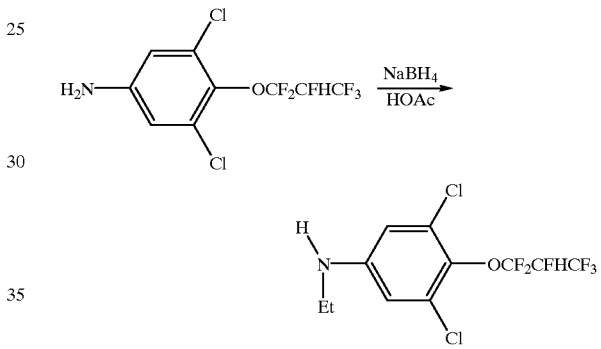

To a solution of 0.33 g 3,5-dichloro-4-(1,1,2,3,3,3-hexafluoropropoxy)aniline in 8 mL glacial acetic acid under an atmosphere of nitrogen at room temperature was slowly added 0.38 g sodium borohydride over a 1.5 hour period through a solid addition funnel between 18–20° C. with ice water cooling. Analysis by thin layer chromatography silica gel 1:1 heptane/ethyl acetate indicated an incomplete reaction. After warming the reaction mixture at 30° C. for two hours, analysis by TLC showed only a faint spot remaining for the starting aniline. The reaction mixture was then added to 100 mL water and the pH was carefully adjusted to 7 by adding solid sodium carbonate. The product was extracted into ethyl acetate 2×80 mL. The ethyl acetate extracts were combined, washed with brine, then dried over magnesium sulfate. The magnesium sulfate was removed by filtering, and the filtrate was concentrated under vacuum to give a brown oil 0.30 g. Chromatograph using a Michel-Miller low pressure silica gel column and elute with 6:1 heptane/ethyl acetate. Pool like fractions and concentrate under vacuum to give 3,5-Dichloro-4-(1,1,2,3,3,3-hexafluoropropoxy)-N-ethyl aniline as a colorless oil 0.17 g. Proton nmr and mass spectra were consistent with the proposed structure. $^{1}$H-NMR d 1.20 (t, 3H), 3.08 (q, 4H), 3.69 (bs, 1H), 4.92–5.22 (md, 1H), 6.48 (s, 2H). MS (CI) m/z 336 (100), 356 (M+H, 100), 384 (M+29, 46).

Compound 1
N-[3,5-Dichloro-4-(1,1,2,3,3,3-hexafluoropropoxy)phenyl]-N'-(2,6-difluorobenzoyl) urea

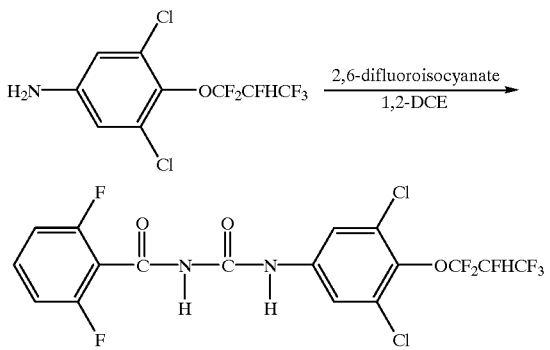

To a solution of 5.13 g 3,5-dichloro-4-(1,1,2,3,3,3-hexafluoropropoxy)aniline in 100 mL 1,2-dichloroethane under an atmosphere of nitrogen at room temperature was added 3.44 g 2,6-difluorobenzoyl isocyanate dissolved in 50 mL dichloroethane dropwise over a 20 minute period between 24°–36° C. with no external cooling. The mixture was heated at 44° C. for 30 minutes. A precipitate formed. The mixture was concentrated under vacuum to dryness and then dissolved in 80 mL boiling methanol. The mixture as filtered and the filtrate concentrated to 30 mL and allowed to cool as product crystallized. Filtration recovered 6.11 g of the title product as a white solid, mp 164–5° C. The proton and $^{19}$F nmr spectra were consistent with the proposed structure. Anal. calcd $C_{17}H_8Cl_2F_8N_2O_3$: C, 39.94; H, 1.58; N, 5.48. Found: C, 39.95; H, 1.60; N, 5.49.

Compound 2
N-[3,5-Dichloro-4-(1,1,2,3,3,3-hexafluoropropoxy)phenyl]-N'-(2,6-difluorobenzoyl)-N'-ethyl urea

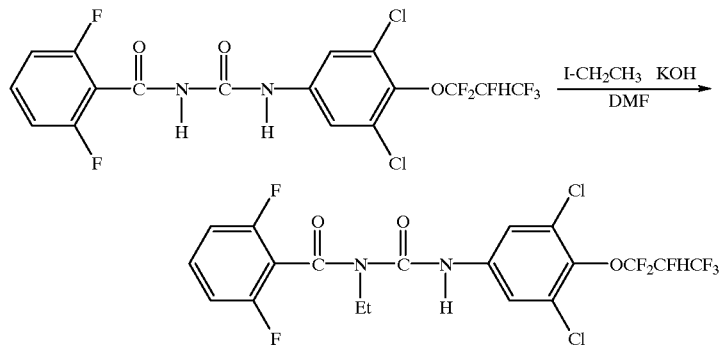

To a solution of 5.00 g N-[3,5-dichloro-4-(1,1,2,3,3,3-hexafluoro-propoxy)phenyl]-N'-(2,6-difluorobenzoyl) urea in 10 mL N,N-dimethylformamide was added 0.69 g 87% potassium hydroxide. The mixture was chilled to 5° C. and 3.05 g of iodoethane were added. After stirring the mixture at 5° C. for one hour, analysis by thin layer chromatography silica gel dichloromethane showed a single product forming with a substantial amount of starting material present. The mixture was allowed to warm to room temperature and was stirred at room temperature for 1.5 hour. Analysis by TLC showed multiple product spots. The mixture was poured into 50 mL brine solution and the pH adjusted to 7.0 with 1N hydrochloric acid. The product was extractred into 80 mL ethyl acetate. The organic layer was separated and dried over magnesium sulfate. Magnesium sulfate was removed by filtration and the filtrate was concentrated under vacuum to give 5.85 g. of an oil. This was chromatographed using a Michel-Miller low pressure silica gel column eluted with 2:1 heptane/dichloromethane. Like fractions were pooled and concentrated under vacuum to give the title compound as a white solid 0.46 g, mp 109–11° C. Proton nmr and mass spectra were consistent with the proposed structure. Anal. calcd $C_{19}H_{12}Cl_2F_8N_2O_3$: C, 42.32; H, 2.24; N, 5.20. Found: C, 42.38; H, 2.27; N, 5.16.

Compound 3
N-[3,5-Dichloro-4-(1,1,2,3,3,3-hexafluoro-propoxy)phenyl]-N'-(2,6-difluorobenzoyl)-N-ethylurea

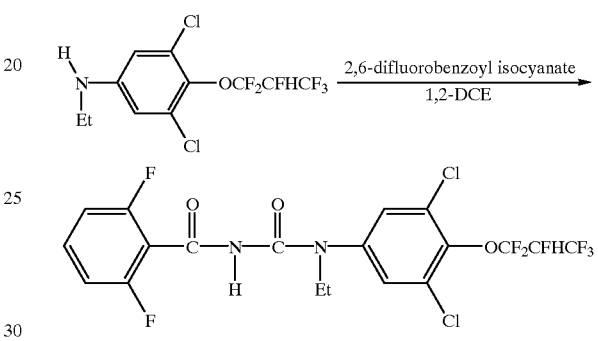

To a solution of 0.17 g 3,5-dichloro-4-(1,1,2,3,3,3-hexafluoropropoxy)-N-ethyl aniline in 0.5 mL 1,2-dichloroethane under an atmosphere of nitrogen at room temperature was added 0.11 g 2,6-difluorobenzoyl isocyanate dissolved in 1.1 mL dichloroethane dropwise over a 5 minute period. The mixture was stirred and warmed to 40° C. for a 2 hour period. Analysis by thin layer chromatography silica gel 4:1 heptane/ethyl acetate indicated no starting aniline remaining. The mixture was stirred at room temperature over night, then concentrated under vacuum to an oil (0.28 g) which solidified. This was chromatographed using a Michel-Miller low pressure silica gel column eluted with 5% ethyl acetate/dichloromethane. Like fractions were pooled and concentrated under vacuum to a white solid 0.11 g, mp 130–33° C. Proton nmr and mass spectra were consistent with the proposed structure. Anal. calcd $C_{19}H_{12}Cl_2F_8N_2O_3$: C, 42.32; H, 2.24; N, 5.20. Found: C, 42.47; H, 2.23; N, 5.08.

Intermediate 4
3,5-dichloro-4-(1,2,3,3,3-pentafluoropropenoxy)aniline

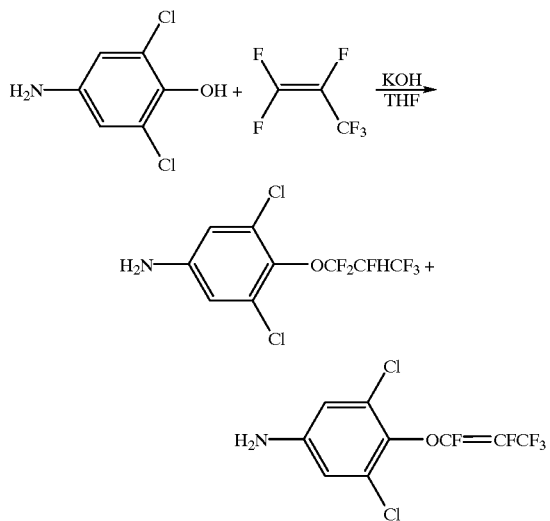

To 1.1 liters of tetrahydrofuran containing 44.5 g of 2,6-dichloro-4-aminophenol and 3.2 g potassium hydroxide, was added subsurface 38.7 g of hexafluoropropene. The addition was complete in 25 minutes at a temperature of 8–11° C. Analysis by liquid chromatography indicates no starting aniline present. Most of the THF was removed under vacuum, 500 mL water was added and the resulting mixture was extracted 3×500 mL ethyl ether. The combined extracts were washed with 2×100 mL 1N NaOH, 2×200 mL brine, dried over anhydrous sodium sulfate, filtered and the solvent removed under vacuum to give a mixture. This mixture was separated by prep LC to give 46.8 g of 3,5-dichloro-4-(1,1,2,3,3,3-hexafluoropropoxy)aniline and ~4 g of 3,5-dichloro-4-(1,2,3,3,3-pentafluoropropenoxy)aniline Proton and $^{19}$F nmr and mass spectra were consistent with the proposed structures.

Intermediate 5
3,5-Dichloro-4-trans-(1,1,2,3,4,4,4-heptafluorobut-2-enoxy) aniline A. Preparation of Sodium Perfluoropentanoate

Perfluoropentanoic acid was(26 g) stirred magnetically as 2N aqueous sodium hydroxide was added dropwise until the pH reached 5. The water was removed under vacuum to yield 28.2 g white solid product, mp 256–7°. The $^{19}$F nmr was consistent with the proposed structure. Anal. Calcd $C_5F_9NaO_2$: C, 21.0. Found: C, 20.89, H, 0.06, N, 0.02.

B. Preparation of Octafluoro-1-butene

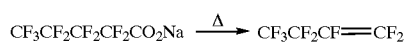

Sodium perfluoropentanoate (28 g) was placed in a 100 ml round-bottom flask and heated with a mantle with no stirring. The flask was fitted with a tube which went through a trap, a 30% aqueous sodium hydroxide bubbler (containing some Dow Corning Antifoam A to control foaming), and a Drierite tube before the product was allowed to bubble into a reaction mixture. Heating was controlled so as to maintain a steady, but not too vigorous rate of bubbling through the trap.

C. Preparation of 3,5-Dichloro-4-trans-(1,1,2,3,4,4,4-heptafluorobut-2-enoxy)aniline

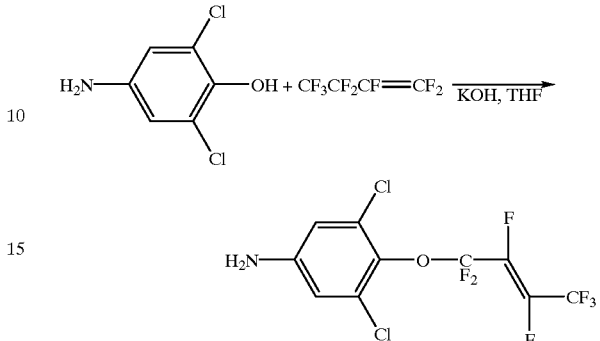

The butene generated in the above reaction was bubbled in subsurface to 14 g 4-amino-3,5-dichlorophenol in 175 ml THF containing 5.15 g 87% powdered potassium hydroxide pellets cooled in an ice bath over 2.5 hours. Stirring was continued while the mixture was allowed to warm to room temperature. The solvent was removed under vacuum and 300 ml dichloromethane was added. This solution was washed with 100 ml water, 100 ml 1N sodium hydroxide, 100 ml 1N HCl, and again with 50 ml 1N NaOH before drying over anhydrous magnesium sulfate. Removed solvent under vacuum to leave a dark oil. This was chromatographed over silica gel starting with 1:1 hexane-dichloromethane and eluting product with dichloromethane. The total yield of nearly colorless oil was 15 g. Anal. calcd $C_{10}H_4Cl_2F_7NO$: C, 33.55; H, 1.13; N, 3.91. Found: C, 33.32; H, 1.12; N, 3.81. Proton and $^{19}$F nmr confirm the olefinic structure as shown with a trans configuration around the double bond.

Compound 4
N-[3,5-Dichloro-4-(1,2,3,3,3-pentafluoropropenoxy)phenyl]-N'-(2,6-difluorobenzoyl)urea

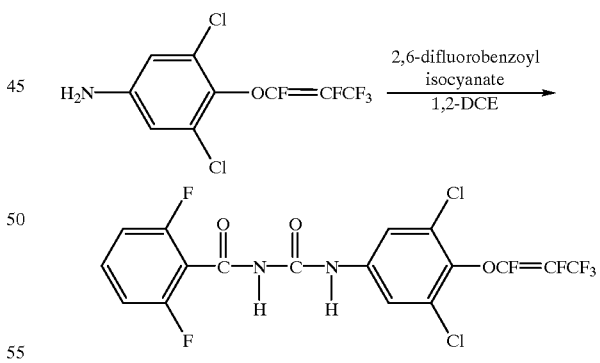

3,5-Dichloro-4-(1,2,3,3,3-pentafluoropropenoxy) aniline (0.77 g) was dissolved in 8 mL 1,2-dichloroethane under an atmosphere of nitrogen at room temperature. To this was added 0.50 g 2,6-difluorobenzoyl isocyanate dissolved in 5.8 mL dichloroethane dropwise over a 10 minute period. The mixture was stirred and warmed to 40° C. for a 2 hour period, then chilled in ice water bath and filter the white solid 0.93 g, mp 177–80° C. Proton nmr and mass spectra were consistent with the proposed structure. Anal. calcd $C_{17}H_7Cl_2F_7N_2O_3$: C, 41.57; H, 1.44; N, 5.70. Found: C, 41.65; H, 1.31; N, 5.59.

Compound 5

1-(2,6-Difluorobenzoyl)-3-[3,5-dichloro-4-trans-(1,1,2,3,4,4,4-heptafluorobut-2-enoxy)phenyl] urea

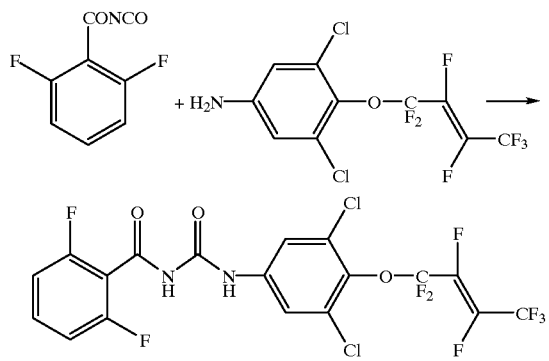

2,6-Difluorobenzoyl isocyanate made from 0.52 g 2,6-difluorobenzamide was stirred in 10 ml 1,2-dichloroethane while 1.08 g of the amine made above in 5 ml 1,2-dichloroethane was added in portions. The mixture was heated to reflux and then cooled. The solvent was removed under vacuum and the resulting solid recrystallized from methanol to give 0.95 g white crystals, mp 153–4°. The proton and $^{19}$F nmr's were consistent with the proposed structure. Anal. calcd $C_{18}H_7Cl_2F_9N_2O_3$: C, 39.95; H, 1.30; N, 5.18. Found: C, 39.65; H, 1.36; N, 5.19.

Biological Data

In the following three experiments, juvenoids, chitin synthesis inhibitors (CSI's), and combinations of the two were evaluated in a continuous-exposure assay employing field-collected eastern subterranean termites (*Reticulitermes flaivipes*). Experimental units were comprised of 35×10 mm sterile disposable petri plates containing 4 ml of sterile 5% bacto-agar, one treated 2.3 cm-diameter filter paper circle (grade 3 Whatman™), and ten worker termites. The agar served as both a water source and tunneling medium for the termites, whereas the treated paper circle served as a food source. Technical-grade juvenoids and CSI's were formulated in acetone to achieve concentrations ranging from 200 to 800 ppm. CSI's tested were lufenuron, diflubenzuron, and hexaflumuron, and juvenoids tested were methoprene and pyriproxyfen. Treatments employed in the assays were: CSI only at 800 ppm, juvenoid only at 800 ppm, CSI+juvenoid at 400 ppm each, CSI+juvenoid at 200 and 600 ppm, respectively, and an acetorne-only control treatment. One-tenth ml of each treatment (or a total of 0.2 ml for combination treatments) were applied to the filter paper circles. After the acetone carrier evaporated from the paper circles (1 hr minimum), the circles were placed on the agar surfaces in the petri plates, and the termites were then placed in the plates. Each treatment was replicated in ten plates. Cumulative termite mortality for each experimental unit was determined at 7, 14, 21, and 28 days of exposure. Analysis of variance and Student-Newman-Keuls test were used to assess treatment effects within each grading period.

Experiment 1.

The impact of combination treatments of lufenuron in combination with various juvenoids on subterranean termites (*Reticulitermes flavipes*, Indianapolis, Ind. colony) was studied.

Results are given in Table 1.

TABLE 1

| Material | Rate (ppm) | Cumulative Percent Mortality * | | | |
|---|---|---|---|---|---|
| | | 7 days | 14 days | 21 days | 28 days |
| lufenuron | 800 | 11 a | 43 b | 68 b | 76 ab |
| methoprene | 800 | 3 a | 3 c | 41 c | 62 b |
| pyriproxyfen | 800 | 0 a | 6 c | 41 c | 75 ab |
| lufenuron + methoprene | 400+ 400 | 25 a | 92 a | 100 a | 100 a |
| lufenuron + methoprene | 200+ 600 | 5 a | 67 b | 99 a | 100 a |
| lufenuron + pyriproxyfen | 400 + 400 | 24 a | 65 b | 96 a | 100 a |
| lufenuron + pyriproxyfen | 200 + 600 | 10 a | 50 b | 100 a | 100 a |
| control | 0 | 2 a | 11 c | 11 d | 12 c |

* Percent mortalities within a column sharing the same letter were calculated from means not differing at the 0.05 level (Student-Newman-Keuls test).

Experiment 2.

The impact of combination treatments of diflubenzuron in combination with various juvenods on subterranean termites (*Reticulitermes flavipes*, Indianapolis, Ind. colony) was studied.

Results are given in Table 2.

TABLE 2

| Material | Rate (ppm) | Cumulative Percent Mortality * | | | |
|---|---|---|---|---|---|
| | | 7 days | 14 days | 21 days | 28 days |
| diflubenzuron | 800 | 31 a | 44 a | 48 a | 60 b |
| methoprene | 800 | 3 b | 3 b | 41 ab | 62 b |
| pyriproxyfen | 800 | 0 b | 6 b | 41 ab | 75 ab |
| diflubenzuron + methoprene | 400+ 400 | 10 b | 32 b | 80 a | 96 a |
| diflubenzuron + methoprene | 200+ 600 | 0 b | 1 b | 79 a | 91 a |
| diflubenzuron + pyriproxyfen | 400 + 400 | 1 b | 12 b | 63 a | 96 a |
| diflubenzuron + pyriproxyfen | 200 + 600 | 0 b | 3 b | 73 a | 94 a |
| control | 0 | 2 b | 11 b | 11 b | 12 c |

* Percent mortalities within a column sharing the same letter were calculated from means not differing at the 0.05 level (Student-Newman-Keuls test).

Experiment 3.

The impact of combination treatments of hexaflumuron in combination with various juvenoids on subterranean termites (*Reticulitermes flavipes*, Indianapolis, Ind. colony) was studied.

Results are given in Table 3.

TABLE 3

| Material | Rate (ppm) | Cumulative Percent Mortality * | | | |
|---|---|---|---|---|---|
| | | 7 days | 14 days | 21 days | 28 days |
| hexaflumuron | 800 | 2 a | 6 a | 15 b | 27 c |
| methoprene | 800 | 3 a | 3 a | 41 b | 62 b |
| pyriproxyfen | 800 | 0 a | 6 a | 41 b | 75 ab |
| hexaflumuron + methoprene | 400+ 400 | 0 a | 1 a | 78 a | 92 a |

TABLE 3-continued

| Material | Rate (ppm) | Cumulative Percent Mortality * | | | |
|---|---|---|---|---|---|
| | | 7 days | 14 days | 21 days | 28 days |
| hexaflumuron + methoprene | 200 + 600 | 0 a | 7 a | 80 a | 92 a |
| hexaflumuron + pyriproxyfen | 400 + 400 | 10 a | 14 a | 72 a | 96 a |
| hexaflumuron + pyriproxyfen | 200 + 600 | 0 a | 9 a | 87 a | 95 a |
| control | 0 | 2 a | 11 a | 11 b | 12 c |

* Percent mortalities within a column sharing the same letter were calculated from means not differing at the 0.05 level (Student-Newman-Keuls test).

The foregoing biological tests demonstrate that termiticide compositions comprising a chitin synthesis inhibitor in combination with a juvenile hormone mimic, in accordance with the invention, consistently give significantly better performance at 21 days and 28 days than would be expected based on results obtained when chitin synthesis inhibitors and juvenile hormone mimics are used alone at similar overall rates.

Formulations

In order to facilitate the application of the combination of active ingredients to the desired locus, or to facilitate storage, transport or handling, the active ingredients are normally formulated with a carrier and/or a surface-active agent.

A carrier in the present context is any material with which the active ingredients are formulated to facilitate application to the locus, or storage, transport or handling. A carrier may be a solid or a liquid, including a material which is normally gaseous but which has been compressed to form a liquid. Any of the carriers normally used or known to be usable in formulating insecticidal compositions may be used.

Compositions according to the invention contain 0.0001 to 99.9% by weight active ingredient. Preferably, compositions according to the invention contain 0.001 to 10.0% by weight of active ingredient though proportions as low as 0.0001% may be useful in some circumstances.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulfur; natural and synthetic resins, for example coumaronne resins, polyvinyl chloride, and styrene polymers and copolymers; solid polychlorophenols; bitumen; waxes; agar; and solid fertilizers, for example super-phosphates. Cellulose based materials, for example wood, sawdust, agar, paper products, cotton linter, or Methocel®, as well as the other solid carriers that are themselves attractive to or at least non-repellant to termites are particularly suitable and preferable. Mixtures of different solids are often suitable. For example, a mixture of wood flour and agar formulated as a moisture containing solid would be preferable. Suitable liquid carriers include water; alcohols, for example isopropanol and glycols; ketones, for example acetone, methyl ethyl ketone, methyl isobutyl ketone, isophorone and cyclohexanone; ethers; aromatic or aliphatic hydrocarbons, for example benzene, toluene and xylene; petroleum fractions, for example kerosene and light mineral oils; chlorinated hydrocarbons, for example carbon tetrachloride, perchloroethylene and trichloroethane; polar organic liquids, such as dimethyl formamide, dimethyl acetamide, dimethyl sulfoxide and N-methylpyrrolidone. Mixtures of different liquids are often suitable, for example a mixture of isophorone with a polar organic solvent such as N-methylpyrrolidone, as are mixtures of solid and liquid carriers. Pesticidal compositions are often formulated and transported in a concentrated form which is subsequently diluted by the user before application. The presence of small amounts of a carrier which is a surface-active agent facilitates this process of dilution. Thus it is suitable to use at least one carrier in such a composition which is a surfaceactive agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sufonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensates of these with ethylene oxide and/or propylene oxide; condensation products of fatty alcohol or alkyl phenols, for example p-octylphenol or p-octylcresol, with ethylene oxide and/or propylene oxide; sulfates or sulfonates of these condensation products; alkali or alkaline earth metal salts, preferably sodium salts, or sulfuric or sulfonic acid esters containing at least 10 carbon atoms in the molecule, for example sodium lauryl sulphate, sodium secondary alkyl sulfates, sodium salts of sulfinated castor oil, and sodium alkylaryl sulfonates such as dodecylbenzene sulfonate; and polymers of ethylene oxide and copolymers of ethylene oxide and propylene oxide. Pesticidal compositions may for example be formulated as wettable powders, dusts, granules, baits, solutions, emulsifiable concentrates, emulsions, suspension concentrates and aerosols.

Wettable powders usually contain 25, 50 or 75% weight of active ingredient and usually contain in addition to solid inert carrier, 3–10% weight of a dispersing agent and, where necessary, 0–10% weight of stabilizer(s) and/or other additives such as penetrants or stickers.

Dusts are usually formulated as a dust concentrate having a similar composition to that of a wettable powder but without a dispersant, and are diluted in the field with further solid carrier to give a composition usually containing 0.5–10% weight of active ingredient.

Granules are usually prepared to have a size between 10 and 100 BS mesh (1.676–0.152 mm), and may be manufactured by, for example, agglomeration or impregnation techniques. Generally, granules will contain 0.01–75% weight active ingredient and 0–10% weight of additives such as stabilizers, surfactants, slow release modifiers and binding agents. The so-called "dry flowable powders" consist of relatively small granules having a relatively high concentration of active ingredient. Of particular interest in current practice are the water dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulation contain 90% or more by weight of finely divided active material, 3–7% by weight of a blend of surfactants, which act as wetting dispersing, suspending and binding agents, and 1–3% by weight of a finely divided carrier, which acts as a resuspending agent. Baits are prepared by, for example, combining a mixture of a finely divided cellulose material, such as sawdust, with an amount of active ingredient sufficient to provide the desired result; for example, from about 0.001% to about 20% weight active ingredient and forming the mixture into a paste by the addition of about 1% to 5% of a water based binder such as agar. The paste-like mixture is packed into a housing such as a hollowed out wooden dowel or a plastic tube. In other embodiments, sheets of paper or cardboard can be sprayed with or dipped in a diluted formulation containing the active ingredient. Baits are a preferable embodiment of the present invention.

Emulsifiable concentrates usually contain, in addition to a solvent and, when necessary, co-solvent, 10–50% weight per volume active ingredient, 2–20% weight per volume emulsifiers and 0–20% weight per volume of other additives such as stabilizers, penetrants and corrosion inhibitors.

Suspension concentrates are usually compounded so as to obtain a stable, non-sedimenting flowable product and usually contain 10–75% weight active ingredient, 0.5–15% weight of dispersing agents, 0.1–10% weight of suspending agents such as protective colloids and thixotropic agents, 0–10% weight of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions are compositions which may be obtained by diluting a wettable powder or a concentrate with water. The said emulsions may be of the water-in-oil or of the oil-in-water type, and may have a thick mayonnaise'-like consistency.

The method of applying compositions of the invention to combat termites comprises applying the compound, conveniently in a composition comprising the active ingredients and a carrier as described above, to a locus or area to be treated for the termites, such as soil or timber, already subject to infestation or attack by termites or intended to be protected from infestation by termites. The active ingredient is, of course, applied in an amount sufficient to effect the desired action of combating termite infestation. This dosage is dependent upon many factors, including the carrier employed, the method and conditions of the application, whether the formulation is present at the locus in the form of a film, or as discrete particles or as a bait, the thickness of film or size of particles, the degree of termite infestation, and the like.

Proper consideration and resolution of these factors to provide the necessary dosage of the active ingredient at the locus to be protected are within the skill of those versed in the art. In general, however, the effective dosage of the compound of the invention at the locus to be protected—i.e., the dosage to which the termite has access—is of the order of 0.001 to 1.0% based on the total weight of the composition, though under some circumstances the effective concentration may be as little as 0.0001% or as much as 2%, on the same basis.

We claim:

1. A method of controlling termites which comprises delivering a composition comprising a chitin synthesis inhibitor in combination with a juvenile hormone mimic to a location where control of termites is desired.

2. A method of claim 1 wherein the chitin synthesis inhibitor is a compound of formula (I):

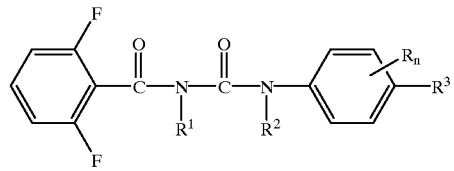

wherein $R^1$ and $R^2$ are H, methyl, or ethyl;

$R_n$ represents H, 2-fluoro, 3,5-dichloro, 2,5-dichloro, or 2-fluoro-3,5-dichloro;

$R_3$ is Cl, or $OR_4$ $R_4$ is (a) $C_nH_mF_{(2n+1-m)}$, where n is 2 to 4 and m is 0 to 2n+1;

(b) $CF=CFCF_3$ or $CF_2CF=CFCF_3$; or (c)

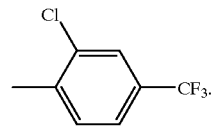

3. A method of claim 2 wherein the chitin synthesis inhibitor is selected from the group consisting of hexaflumuron, flufenoxuron, lufenuron, and dimilin.

4. A method of claim 3 wherein the juvenile hormone mimic is selected from the group consisting of methoprene and pyriproxyfen.

5. A method of claim 1 wherein the juvenile hormone mimic is selected from the group consisting of methoprene and pyriproxyfen.

6. A method of claim 1 wherein the chitin synthesis inhibitor and juvenile hormone mimic are present in a ratio of 1:1 to 1:3.

7. A method of controlling termites which comprises delivering a termite bait comprising a chitin synthesis inhibitor in combination with a juvenile hormone mimic and a bait matrix to a location where control of termites is desired.

8. A method of claim 7 wherein the bait matrix comprises a cellulose material.

9. A method of claim 7 wherein the bait matrix comprises a paper product.

* * * * *